US 12,305,197 B2

(12) United States Patent
Onishi et al.

(10) Patent No.: US 12,305,197 B2
(45) Date of Patent: May 20, 2025

(54) PROLIFERATION METHOD

(71) Applicants: Kao Corporation, Tokyo (JP); Shizuoka Prefectural University Corporation, Shizuoka (JP)

(72) Inventors: Shintaro Onishi, Taito-ku (JP); Takuya Mori, Utsunomiya (JP); Takashi Suzuki, Shizuoka (JP); Yuuki Kurebayashi, Shizuoka (JP)

(73) Assignees: Kao Corporation, Tokyo (JP); Shizuoka Prefectural University Corporation, Shizuoka (JP)

( * ) Notice: Subject to any disclaimer, the term of this patent is extended or adjusted under 35 U.S.C. 154(b) by 928 days.

(21) Appl. No.: 17/429,454

(22) PCT Filed: Feb. 7, 2020

(86) PCT No.: PCT/JP2020/004930
§ 371 (c)(1),
(2) Date: Aug. 9, 2021

(87) PCT Pub. No.: WO2020/166524
PCT Pub. Date: Aug. 20, 2020

(65) Prior Publication Data
US 2022/0127582 A1    Apr. 28, 2022

(30) Foreign Application Priority Data

Feb. 14, 2019   (JP) .................................. 2019-024777
Dec. 16, 2019   (JP) .................................. 2019-226747

(51) Int. Cl.
| C12N 7/00 | (2006.01) |
| A61K 39/00 | (2006.01) |
| A61K 39/145 | (2006.01) |
| C12N 5/071 | (2010.01) |
| C12N 5/073 | (2010.01) |

(52) U.S. Cl.
CPC .............. *C12N 7/00* (2013.01); *A61K 39/145* (2013.01); *C12N 5/0604* (2013.01); *C12N 5/0684* (2013.01); *A61K 39/00* (2013.01); *A61K 2039/5258* (2013.01); *C12N 2760/16123* (2013.01); *C12N 2760/16134* (2013.01); *C12N 2760/16223* (2013.01); *C12N 2760/16234* (2013.01)

(58) Field of Classification Search
None
See application file for complete search history.

(56) References Cited

U.S. PATENT DOCUMENTS

| 2009/0181446 A1 | 7/2009 | Nouchi et al. |
| 2010/0003756 A1 | 1/2010 | Collingwood et al. |
| 2014/0256039 A1 | 9/2014 | Matsuyama |

FOREIGN PATENT DOCUMENTS

| JP | 2005-320276 A | 11/2005 |
| JP | 2011-522564 A | 8/2011 |
| WO | WO 2007/132763 A1 | 11/2007 |
| WO | WO 2009/151591 A2 | 12/2009 |

OTHER PUBLICATIONS

Rivas-Carrillo, et al. Diabetes. May 2007;56(5):1259-67. doi: 10.2337/db06-1679. Epub Feb. 7, 2007. PMID: 17287463. (Year: 2007).*
Hossain, et al. Int J Mol Sci. Mar. 2, 2018;19(3):712. doi: 10.3390/ijms19030712. PMID: 29498634. (Year: 2018).*
Ishikawa, et al. Cell Death Differ. Aug. 2011;18(8):1271-8. doi: 10.1038/cdd.2011.59. Epub May 20, 2011. PMID: 21597463. (Year: 2011).*
McLean JE et al., "Lack of Bax prevents influenza A virus-induced apoptosis and causes diminished viral replication." J Virol. Aug. 2009;83(16):8233-46. doi: 10.1128/JVI.02672-08. Epub Jun. 3, 2009. PMID: 19494020; PMCID: PMC2715773.
The extended European search report, including the supplementary European search report and the European search opinion, dated Oct. 28, 2022, for EP Application No. 20754881.9, the European Patent Office, Munich, Germany.
International Search Report for PCT/JP2020/004930; I.A. fd Feb. 7, 2020, mailed Apr. 28, 2020 from the Japan Patent Office, Tokyo, Japan.
International Preliminary Report on Patentability (IPRP), Chapter I of the Patent Cooperation Treaty, including the Written Opinion, for PCT/JP2020/004930; I.A. fd Feb. 7, 2020, issued Aug. 10, 2021, by the International Bureau of WIPO, Geneva, Switzerland.
Tobita, K, et al., "Plaque assay and primary isolation of influenza A viruses in an established line of canine kidney cells (MDCK) in the presence of trypsin." Med Microbiol Immunol. Dec. 30, 1975;162(1):9-14. doi: 10.1007/BF02123572. PMID: 1214709.
Wurzer, WJ, et al. "Caspase 3 activation is essential for efficient influenza virus propagation." EMBO J. Jun. 2, 2003;22(11):2717-28. doi: 10.1093/emboj/cdg279. PMID: 12773387; PMCID: PMC158404.
Hossain, MK, et al., "Bax Inhibitor-1 Acts as an Anti-Influenza Factor by Inhibiting ROS Mediated Cell Death and Augmenting Heme-Oxygenase 1 Expression in Influenza Virus Infected Cells." Int J Mol Sci. Mar. 2, 2018;19(3):712. doi: 10.3390/ijms19030712. PMID: 29498634; PMCID: PMC5877573 (15 pages).

(Continued)

*Primary Examiner* — Janet L Andres
*Assistant Examiner* — Jeffrey Mark Sifford
(74) *Attorney, Agent, or Firm* — Sterne, Kessler, Goldstein & Fox P.L.L.C.

(57) ABSTRACT

Provided is a method for efficiently proliferating an influenza virus serving as a material for vaccine in a host.

A method for proliferating an influenza virus in a host, comprising a step of inhibiting transfer of Bax in a host cell to the inner mitochondrial membrane.

9 Claims, 8 Drawing Sheets

Specification includes a Sequence Listing.

(56) References Cited

OTHER PUBLICATIONS

Manzur, M. et al., "Virally mediated inhibition of Bax in leukocytes promotes dissemination of murine cytomegalovirus." Cell Death Differ. Feb. 2009;16(2):312-20. doi: 10.1038/cdd.2008.152. Epub Oct. 24, 2008. PMID: 18949000.

* cited by examiner

PROLIFERATION METHOD

FIELD OF THE INVENTION

The present invention relates to a method for proliferating an influenza virus in a host.

BACKGROUND OF THE INVENTION

Influenza is an infection caused by influenza viruses, which is transmitted through droplet infection, and is a respiratory infection, and the like accompanying strong systemic symptoms such as high fever, headache, muscle pain, and joint pain. Influenza vaccination is the best means to prevent an increase in the severity of influenza.

The influenza vaccine is a whole-virus vaccine obtained by inoculating an influenza virus for vaccine production into the allantoic cavity of embryonated chicken eggs to culture and proliferate, concentrating and purifying the allantoic fluid by centrifugation, treating virus particles with a surfactant and the like, and inactivating them with formalin; a split vaccine or a subunit vaccine prepared by disintegrating virus particles with an ether or a surfactant and then further performing purification. However, when the influenza vaccine is produced using chicken eggs with embryos as a host, there are problems in terms of supply stability in that time, labor, and money are required and immediate mass production is impossible.

As an alternative virus production method, an approach to replicate viruses using cultured cells as a host of influenza virus has been studied, and it is reported that MDCK cells are suitable to replicate influenza viruses in vitro (Non Patent Literature 1). Patent Literature 1 also discloses that the amount of virus produced can be increased by removing or reducing a trypsin inhibitor secreted in the culture solution of MDCK cells, and then inoculating the cells with an influenza virus to culture influenza virus-inoculated cells.

Non Patent Literature 2 discloses that avian influenza viruses (A/Bratislava/79 (H7N7)) is efficiently propagated by being transported out of the nucleus by use of biological defense function (apoptosis), and suggests that the apoptosis of cultured cells is involved in the proliferation of influenza virus.
(Patent Literature 1) WO 2007/132763
(Non Patent Literature 1) Med Microbiol Immunol (1975) 162, 9-14
(Non Patent Literature 2) THE EMBO Journal (2003)22, 2717-2728

SUMMARY OF INVENTION

The present invention relates to the following 1) to 5).
1) A method for proliferating an influenza virus in a host, comprising a step of inhibiting transfer of Bax in a host cell to an inner mitochondrial membrane.
2) A method for preparing influenza virus particles, comprising proliferating an influenza virus according to the method according to 1), and collecting virus particles from the host.
3) An influenza virus proliferation-promoting agent comprising a Bax inhibitor as an active ingredient.
4) Use of a Bax inhibitor for promoting proliferation of an influenza virus.
5) Use of a Bax inhibitor for producing an influenza virus proliferation-promoting agent.

DESCRIPTION OF EMBODIMENTS

The present invention relates to provide a method for efficiently proliferating an influenza virus serving as a material for vaccine in a host.

The present inventors conducted extensive studies and as a result, found that when the transfer of Bax, known as a pro-apoptotic protein, to the inner mitochondrial membrane is inhibited to inhibit apoptosis in a host to be infected with an influenza virus, the virus proliferation capacity is improved and the amount of virus produced is increased, unlike the previous reports.

According to the present invention, the influenza virus can be efficiently proliferated and the influenza virus for preparing a vaccine therefor can be mass-produced.

In the present invention, the influenza virus may be any of type A, type B, type C, and type D, and preferred examples include type A and type B.

The type of haemagluttinin (erythrocyte agglutinin, HA) (HA type) and the type of neuraminidase (NA type) of the influenza virus is not particularly limited. Examples thereof include not only currently known subtypes such as H1N1 strains, H2N2 strains, H3N2 strains, H4N2 strains, H4N6 strains, H5N1 strains, H5N2 strains, H7N7 strains, H7N9 strains, and H9N2 strains, but also subtypes which will be isolated and identified in the future.

The virus to be subjected may be any virus which can infect humans, or may be any virus which has an ability to infect pigs, birds, horses, and cattle.

The influenza virus of the present invention may be a strain isolated from an infected individual such as an infected animal and patient, or may be a recombinant virus established in a cultured cell in a genetic engineering manner.

In the present invention, "Bax" refers to a pro-apoptotic protein belonging to the Bcl-2 family. The protein belonging to the Bcl-2 family has one or more amino acid sequences called BH (Bcl-2 homology) domain. Since Bax has a highly hydrophobic TM (transmembrane) region on the C-terminal side, Bax can transfer onto the mitochondrial membrane and can control apoptosis.

The main function of the Bcl-2 family protein is the control of apoptosis through modulation of mitochondrial permeability. Anti-apoptotic proteins, Bcl-2 and Bcl-xL are present on the outer wall of the mitochondria and inhibit the release of cytochrome c. Pro-apoptotic proteins, Bad, Bid, Bax, and Bim are present in the cytoplasm, moves to the inner mitochondrial membrane by a signal for cell death, where they promote the release of cytochrome c. It is believed that the cytochrome c flown outside the cells forms a composite with Apaf-1, activates caspase 9, and further activates caspase 3, 6, and 7, thereby causing apoptosis (Annu Rev Genet (2009) 43: 95-118).

In the present invention, "inhibition of transfer of Bax to the inner mitochondrial membrane" refers to inhibit transfer of Bax from the cytoplasm to the inner mitochondrial membrane, resulting from signaling which occurs in a cell during the process of viral infection to release.

The inhibition means is not particularly limited, as long as the transfer of Bax present in the cytoplasm of a host to the inner mitochondrial membrane can be inhibited. Examples thereof include applying a molecule that interacts with Bax and inhibits the mitochondria transfer of Bax (referred to as the "Bax inhibitor") to the cell, and reducing Bax present in the cytoplasm in a genetic engineering manner, and suitable examples thereof includes use of the Bax inhibitor. That is, in the present invention, it can be said that the Bax inhibitor serves as an influenza virus proliferation-promoting agent for proliferating the influenza virus by culture of the host, and can be used to proliferate the influenza virus by culture of the host. It can also be said that the Bax inhibitor can be used to produce the influenza virus proliferation-promoting agent.

Suitable examples of the Bax inhibitor include peptides and compounds which inhibit the binding of Ku70 protein, which is necessary for the transfer of Bax to the inner mitochondrial membrane, to Bax, and examples thereof include peptides described in Biochem Biophys Res Commun (2004)321:961-966) and Nat Cell Biol (2003)5:352-357).

Specific examples thereof include Val-Pro-Met-Leu-Lys (SEQ ID NO: 1), Pro-Met-Leu-Lys-Glu (SEQ ID NO: 2), Val-Pro-Thr-Leu-Lys (SEQ ID NO: 3), and Val-Pro-Ala-Leu-Arg (SEQ ID NO: 4), and also include Val-Pro-Ala-Leu-Lys (SEQ ID NO: 5), Pro-Ala-Leu-Lys-Asp (SEQ ID NO: 6), Val-Ser-Ala-Leu-Lys (SEQ ID NO: 7), and Ser-Ala-Leu-Lys-Asp (SEQ ID NO: 8).

The Bax inhibiting effect by such a Bax inhibitor can be evaluated by, for example, measuring the inhibitory activity on the binding of Bax to Ku70 protein. Also, it can be evaluated by inducing apoptosis in the cells and evaluating the proportion of the apoptotic cells under the conditions where the Bax inhibitor is added.

The Bax inhibitor is used at a concentration of 1 μM or more, preferably 5 μM or more, more preferably 10 μM or more, and 1,000 μM or less, preferably 500 μM or less, more preferably 200 μM or less, and from 1 to 1,000 μM, preferably from 5 to 500 μM, more preferably from 10 to 200 μM, relative to the host for proliferating the influenza virus (type A, type B, type C, or type D).

The proliferation of influenza virus is specifically performed by a step of infecting an influenza virus in a host and a step of culturing the infected host under the conditions where the virus can replicate, but in the present invention, the step of inhibiting transfer of Bax to the inner mitochondrial membrane is performed, for example, before viral infection, after viral infection, or simultaneously with viral infection. Suitable examples thereof include adding the Bax inhibitor to the host before viral infection, after viral infection, or simultaneously with viral infection.

The host to be used for the proliferation of influenza virus may be any of a cultured cell or an embryonated chicken egg, but a cultured cell is preferably used in terms of supply stability.

As the cultured cell, any cells can be used as long as they are susceptible to the influenza virus. Examples of such cells include MDCK cells (a cell line derived from canine kidney), Vero cells (a cell line derived from African green monkey kidney), PER.C6 (a cell line derived from human retinal cells), SK-NEP-1 cells (a cell line derived from human kidney), A549 (an adenocarcinomic human alveolar basal epithelial cell), and Duck embryonic cells. These cells are registered in ATCC (American Type Culture Collection) as CCL-34, CCL-81, CCL-107, HTB-48, CCL-185, and CCL-141, respectively, and can be commercially purchased. Also, CEF cells (chicken embryonic fibroblast cell) can be used as the cells derived from chickens susceptible to the influenza virus. The CEF cells include not only isolated cells but also cells present in embryonated chicken eggs. In addition to these, cell lines developed to efficiently proliferate influenza viruses can be used for the proliferation of influenza virus. Examples of such cell lines include, but are not limited to, EB66®, DuckCelt-T17®, and EBx®.

When cultured cells are used as the host, examples of a culture medium for culturing cells include culture media usually used in cell culture such as an MEM culture medium containing fetal bovine serum (FBS) (manufactured by Wako Pure Chemical Industries, Ltd.) and a serum-free medium (manufactured by Thermo Fisher Scientific Inc.), and any of them may be used.

To increase the proliferation efficiency of the cell, a non-essential amino acid or L-glutamine can be added to the culture medium. In addition, in the culture of the influenza virus, proteases such as trypsin and acetylated trypsin can be added to promote the cleavage of haemagluttinin. To avoid the contamination of microbes, antibiotics that can be commonly used in cell culture, such as penicillin, streptomycin, and gentamicin may be added. The pH of the culture medium is adjusted to pH 6.5 to 8, preferably pH 6.8 to 7.3, which is suitable for the proliferation of animal cell, with an appropriate buffer (e.g., sodium bicarbonate and HEPES).

Examples of the method of cell culture include static culture performed by attaching cells on the bottom of the culture vessel, and suspension culture in which cells are suspended and cultured in the culture medium, but when culture is performed in industrial scale production, suspension culture is preferred. Examples of the method of suspension culture include a method for attaching cells to a carrier such as a microcarrier and suspending and culturing this, or a method for suspending and culturing cells without using any carrier, and either method may be used.

The cell culture (a mixture of cultured cells and the culture medium) may be used for inoculation of the influenza virus as it is, but in inoculation of the influenza virus, cell washing is preferably performed with a fresh culture medium or an appropriate buffer such as PBS and Tris buffer.

Specifically, culture medium exchange is performed by subjecting the cells cultured and proliferated in a spinner flask and the like to centrifugation at a low speed or membrane filtration to separate the cells from culture supernatant, and adding a fresh culture medium to the cells in the precipitate after centrifugation or the concentrate after membrane filtration to suspend the cells.

To the cell culture thus obtained, an influenza virus solution is added, which is cultured under certain conditions. The initial cell density at the start of the virus culture may be from 0.001 to $100\times10^6$ cells/mL, and is preferably from 0.01 to $10\times10^6$ cells/mL, and more preferably from 0.1 to $10\times10^6$ cells/mL. Measurement of the cell density may be performed according to a common method such as a method with a hemocytometer. The influenza virus solution to be added to the cell culture may be added so that its infectivity titer MOI (multiplicity of infection) can be from 0.00001 to 10, and it can be preferably added at an infectivity titer MOI of from 0.0001 to 0.1, and more preferably 0.0001 to 0.01.

When embryonated chicken eggs are used as the host, chicken eggs grown by incubating under the conditions of from 33° C. to 38° C., preferably from 35 to 37° C., and under humidity conditions of from 40 to 60%, preferably from 45 to 55%, and by turning the eggs from 1 to 24 times, preferably from 4 to 12 times a day can be used. The 8- to 13-day old embryonated chicken eggs can be infected with the influenza virus, and preferably, 10- to 12-day old chicken eggs can be infected therewith. For the amount of infected virus, the eggs can be infected with a 50% egg infection dose ($EID_{50}$) of from 1 to $1\times10^6$ $EID_{50}$/Egg, preferably from $1\times10^2$ to $1\times10^5$ $EID_{50}$/Egg, and more preferably from $1\times10^3$ to $1\times10^4$ $EID_{50}$/Egg. The infection site is desirably in the allantoic membrane (in the allantoic fluid) of chicken eggs, may be in the amniotic membrane (in the amniotic fluid), and is not limited as long as it is a site in chicken eggs where the influenza virus is proliferated.

The culture conditions may be any conditions as long as the influenza virus can be proliferated in the host. The conditions may be appropriately regulated depending on the combinations of the type of cells, the amount of viral inoculation, and the scale and method of culture, and the like. For example, when cultured cells are used as the host, the culture temperature is from 33° C. to 39° C., preferably from 34 to 38° C., the culture period is from 1 to 10 days, preferably from 3 to 7 days, the carbon dioxide concentration is from 3 to 8%, preferably from 4 to 5%, and the oxygen concentration is from 17 to 25%, preferably from 20 to 22%.

When embryonated chicken eggs are used as the host, they are cultured after infection under the conditions of from 33° C. to 38° C., preferably from 34 to 36° C., the culture period of from 1 to 5 days, preferably from 2 to 4 days, and the humidity conditions of from 40 to 60%, preferably from 45 to 55%, but the culture period, the culture temperature, the humidity, and the like may be appropriately combined because the conditions at which the proliferation capacity is enhanced to the maximum vary depending on the virus strain.

According to the present invention, the influenza virus can be efficiently proliferated. The content of virus in the host can be measured by hemagglutination methods (dilution factor) using red blood cells of guinea pig and the like, ELISA using antibodies against haemagluttinin (μg/mL), plaque assays to measure infectivity titer, $TCID_{50}$, real-time PCR which can measure the amount of viral RNA, and the like.

The influenza virus is contained in the fluid inside the allantoic membrane (allantoic fluid) or the amniotic fluid when the host is embryonated chicken eggs, and contained in the culture supernatant when the host is cultured cells. After completion of the culture, virus particles are collected from the virus suspension in the host, concentrated, purified, and inactivated, thereby preparing virus particles for inactivated whole-virus vaccines and inactivated split vaccines. When used as live vaccines, live attenuated vaccines, and the like, the virus particles may be concentrated, purified, and then prepared as virus particles for influenza vaccines.

The collection of virus particles may be performed by clarifying the virus suspension, specifically performed by centrifugation or filtration, and then ultrafiltration is performed for concentration. The purification of the virus can be performed using means including ultracentrifugation such as sucrose density gradient centrifugation, and liquid chromatography. The purified viral solution is inactivated by formalin treatment, ultraviolet irradiation, beta propiolactone, binary ethylenimine, and the like, in the cases of whole-virus vaccines and inactivated split vaccines. When used as live vaccines or live attenuated vaccines, the above purified viral solution is prepared as virus particles for influenza vaccines.

Vaccines of various forms can be prepared by appropriately adding pharmaceutically acceptable carriers (buffers, emulsifying agents, preservatives (e.g., thimerosal), isotonic agents, pH regulators, adjuvants (e.g., aluminum hydroxide gel), and the like) to such influenza virus particles.

In relation to the aforementioned embodiments, the present invention further discloses the following aspects.

<1> A method for proliferating an influenza virus in a host, comprising a step of inhibiting transfer of Bax in a host cell to an inner mitochondrial membrane.

<2> The method according to <1>, wherein the step of inhibiting transfer of Bax to the inner mitochondrial membrane is a step of adding a Bax inhibitor to the cell.

<3> The method according to <2>, wherein the Bax inhibitor is a peptide selected from the group consisting of Val-Pro-Met-Leu-Lys (SEQ ID NO: 1), Pro-Met-Leu-Lys-Glu (SEQ ID NO: 2), Val-Pro-Thr-Leu-Lys (SEQ ID NO: 3), Val-Pro-Ala-Leu-Arg (SEQ ID NO: 4), Val-Pro-Ala-Leu-Lys (SEQ ID NO: 5), Pro-Ala-Leu-Lys-Asp (SEQ ID NO: 6), Val-Ser-Ala-Leu-Lys (SEQ ID NO: 7), and Ser-Ala-Leu-Lys-Asp (SEQ ID NO: 8).

<4> The method according to any one of <1> to <3>, wherein the host is a cultured cell or an embryonated chicken egg.

<5> The method according to <4>, wherein the cell is an MDCK cell (a cell line derived from canine kidney), a Vero cell (a cell line derived from African green monkey kidney), PER.C6 (a cell line derived from human retinal cells), an SK-NEP-1 cell (a cell line derived from human kidney), A549 (an adenocarcinomic human alveolar basal epithelial cell), and a Duck embryonic cell, or a chicken embryonic fibroblast cell.

<6> The method according to any one of <2> to <5>, wherein the Bax inhibitor is used at a concentration of 1 μM or more, preferably 5 μM or more, more preferably 10 μM or more, and 1,000 μM or less, preferably 500 μM or less, more preferably 200 μM or less, and from 1 to 1,000 M, preferably from 5 to 500 μM, more preferably from 10 to 200 μM, relative to the host for proliferating an influenza virus (type A, type B, type C, or type D).

<7> A method for preparing influenza virus particles, comprising proliferating an influenza virus according to the method according to any one of <1> to <5>, and collecting virus particles from the host.

<8> The method according to <7>, wherein the virus particles are used for influenza vaccine preparation.

<9> An influenza virus proliferation-promoting agent comprising a Bax inhibitor as an active ingredient.

<10> Use of a Bax inhibitor for promoting proliferation of an influenza virus.

<11> Use of a Bax inhibitor for producing an influenza virus proliferation-promoting agent.

<12> The agent according to <9> or the use according to <10> or <11>, wherein the Bax inhibitor is a peptide selected from the group consisting of Val-Pro-Met-Leu-Lys (SEQ ID NO: 1), Pro-Met-Leu-Lys-Glu (SEQ ID NO: 2), Val-Pro-Thr-Leu-Lys (SEQ ID NO: 3), Val-Pro-Ala-Leu-Arg (SEQ ID NO: 4), Val-Pro-Ala-Leu-Lys (SEQ ID NO: 5), Pro-Ala-Leu-Lys-Asp (SEQ ID NO: 6), Val-Ser-Ala-Leu-Lys (SEQ ID NO: 7), and Ser-Ala-Leu-Lys-Asp (SEQ ID NO: 8).

EXAMPLES

Example 1 Evaluation Test for Virus Proliferation Capacity Using Cell Line Derived from Canine Renal Tubular Epithelial Cells (MDCK Cells)

(1) MDCK cells (a cell line derived from canine renal tubular epithelial cells, obtained from DS Pharma Biomedical Co., Ltd.) were cultured in an MEM culture medium containing 5% fetal bovine serum (FBS) (manufactured by Wako Pure Chemical Industries, Ltd.) at 37° C. under 5% $CO_2$. The above MDCK cells were seeded in a 24-well plate, which were used for the test in a confluent state. The above MDCK cells seeded in the 24-well plate were washed with PBS, and then a serum free medium (SFM; manufactured by Gibco) was added at 400 μL/well, followed by conditioning for 1 hour.

Figure 1:
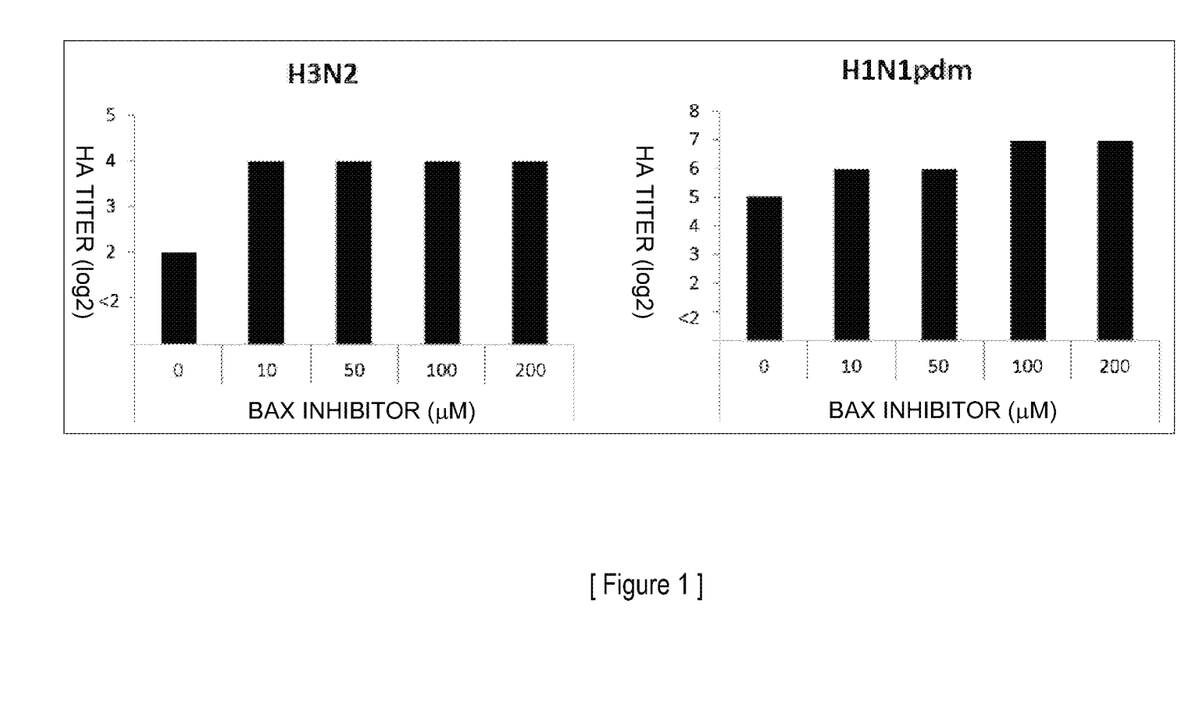
FIG. 1 shows the influenza virus HA titer under various Bax inhibitor concentration conditions.

(2) The above cells were infected with an H3N2 influenza virus strain (A/Memphis/l/1971) and an H1N1pdm influenza virus strain (A/Shizuoka/830/2009), which are influenza A viruses, so that the infectivity titer MOI (multiplicity of infection)=0.001, and incubated for 1 hour. Thereafter, the washing procedure with SFM was performed, and an SFM culture medium containing 2.0 μg/mL-acetylated trypsin (manufactured by Sigma) and added with a Bax inhibitor (Bax inhibitor peptide (V5) (Val-Pro-Met-Leu-Lys (SEQ ID NO: 1); manufactured by TOCRIS bioscience)) at a concentration of 0 to 200 μM was added in an amount of 500 μL/well, followed by culturing for 23 hours. After 24 hours from infection, the culture supernatant was collected, and the HA titer of the influenza viruses was measured by the HA assay described below (FIG. 1). In subsequent experiments, an SFM culture medium containing 2.0 μg/mL-acetylated trypsin was used for culturing influenza viruses in the tests for evaluating the proliferation capacity of influenza viruses.

(3) HA Assay

50 μL of influenza virus culture supernatant was diluted in 2-fold increments from 2 to 1,024-fold using U-bottom 96-well plates to prepare dilution series. 50 μL of PBS containing 0.7% guinea pig red blood cells was added thereto, which was allowed to stand at 4° C. for 2 hours. Thereafter, the agglutination of the red blood cells was checked, and the dilution concentration at which no agglutination was observed was determined as the HA titer.

(4) The results of this examination demonstrated that the addition of the Bax inhibitor increases the HA titer of the H3N1 and H1N1 influenza virus strains.

Figure 2:
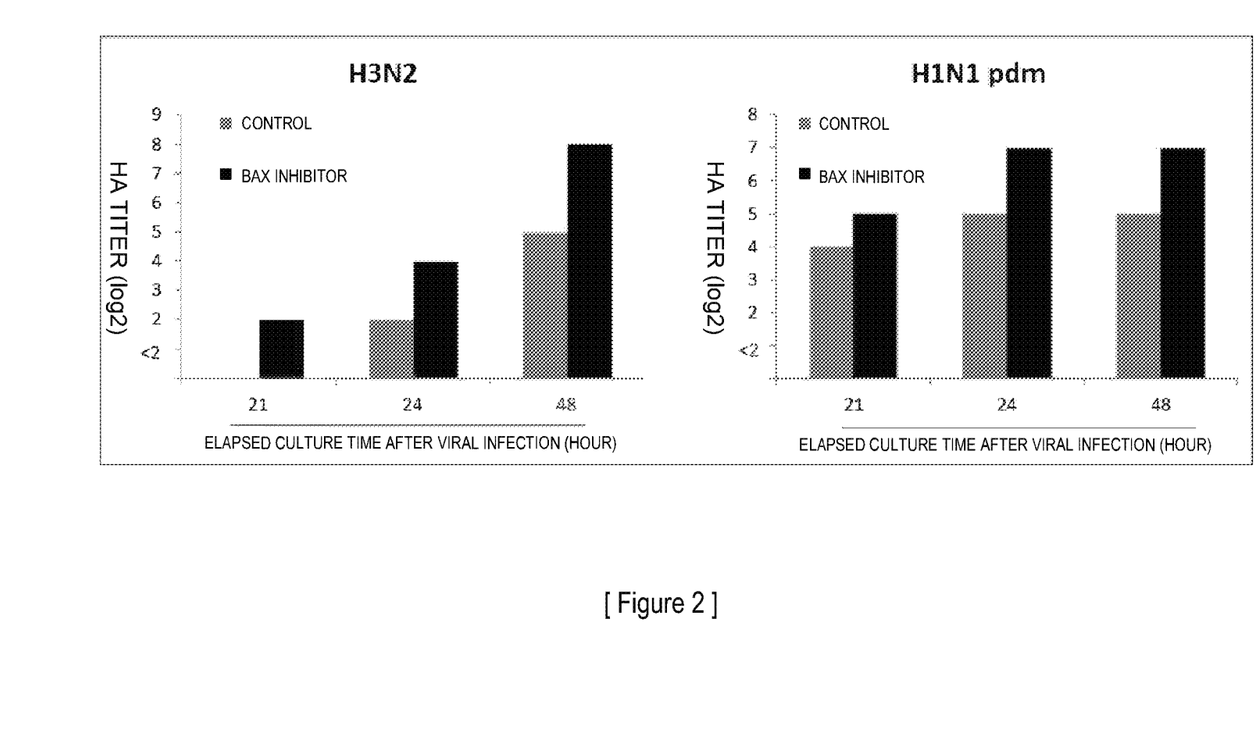
FIG. 2 shows the time-dependent influenza virus HA titer under Bax inhibiting conditions.

Example 2 Examination of Effect of Promoting Proliferation of Influenza Virus Caused by Addition of Bax Inhibitor at Various Time Points (1) As in Example 1, MDCK cells were conditioned with SFM for 1 hour, and then infected with H3N2 and H1N1pdm influenza virus strains so that the infectivity titer MOI=0.001, and incubated for 1 hour. Thereafter, the washing procedure with SFM was performed, a Bax inhibitor (Bax inhibitor peptide (V5)) was added at a concentration of 100 μM, which was cultured for 20 to 47 hours. The culture supernatant was collected at 21 hours, 24 hours, and 48 hours after infection, and the HA titer of the influenza viruses was measured by HA assay (FIG. 2).

The results of this examination demonstrated that the addition of the Bax inhibitor increases the HA titer of the influenza virus strains in the early stages of the culture.

Figure 3:
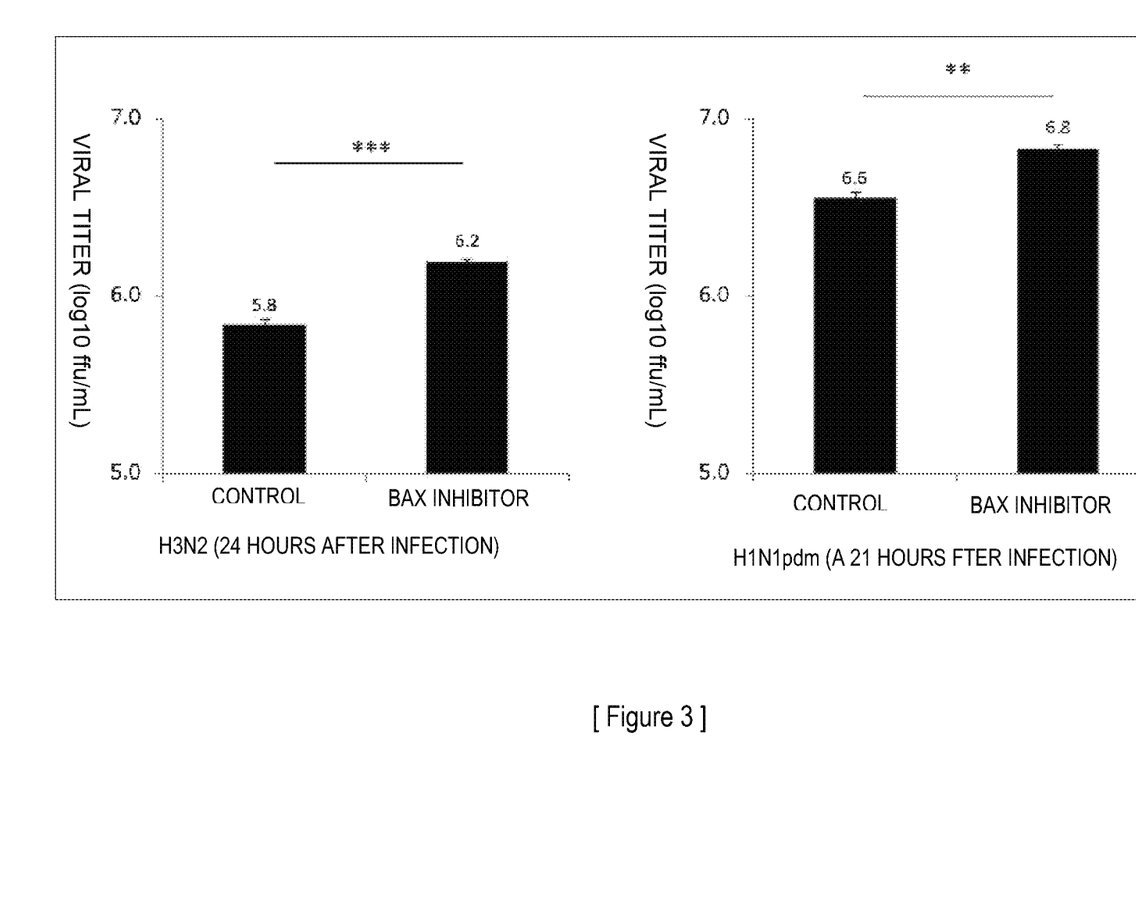
FIG. 3 shows the effect of enhancing the proliferation capacity of influenza virus under Bax inhibiting conditions.

(2) The amount of influenza virus in the culture solution was quantified by the focus assay described below using the culture supernatant at 21 or 24 hours after infection (FIG. 3).

1) Focus Assay

MDCK cells were cultured in a 12-well plate to reach confluency, washed with PBS, and then conditioned with SFM for 1 hour. The influenza virus culture supernatant collected at 21 or 24 hours after infection was diluted 100 to 100,000-fold, added to the MDCK cells cultured in the above 12-well plate at 1 mL/well, and incubated for 1 hour, thereby infecting the cells with influenza virus. This test was performed in triplicate. After infection, the washing procedure with SFM was performed, SFM containing 1.2%-Ceolus (Asahi Kasei Chemicals Corporation, RC591) and 2.0 μg/mL-acetylated trypsin (manufactured by Sigma) was added at 2.0 mL/well, followed by culturing for 30 hours. After culture, the well was washed three times with PBS cooled to 4° C., and then 100% methanol cooled to −20° C. (manufactured by Wako Pure Chemical Industries, Ltd.) was added to immobilize the cells. The immobilized cells were allowed to react with the primary antibody: Anti-NP antibody (mouse hybridoma (4E6) cell culture supernatant: Journal of Virology (2008) 82:5940-5950) and the secondary antibody: HRP linked goat Anti-mouse IgG+IgM antibody (manufactured by Jackson Immuno Research Laboratories, Inc.), allowed to react with HRP using a DEPDA reaction, and the number of stained foci was counted. The focus assay was performed in independent triplicates, statistical analysis was performed using Student's t-test (FIG. 3 and FIG. 5) or one-way analysis of variance (subsequently Tukey test, FIG. 7), by defining 5% risk as the significance level (*; $p<0.05$, ; $p<0.01$, *; $p<0.001$).

2) The results of this examination demonstrated that the addition of the Bax inhibitor exhibits the effect of enhancing the virus proliferation capacity of H3N2 and H1N1 influenza virus strains.

Figure 4:
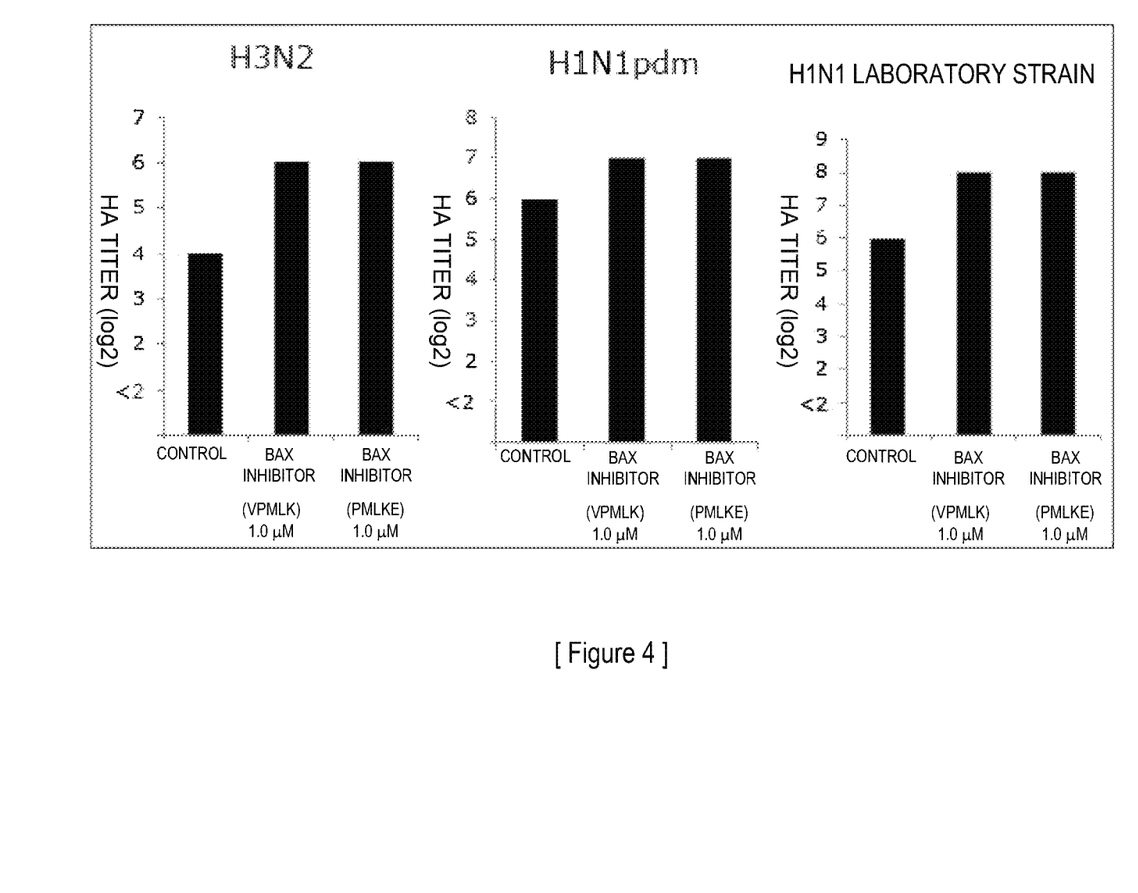
FIG. 4 shows the influenza virus HA titer under low Bax inhibitor concentration conditions.

Example 3 Examination of Effect of Promoting Proliferation of Influenza Viruses Under Condition of Low Bax Inhibitor (2 Types) Concentration (1) As in Example 1, MDCK cells were conditioned with SFM for 1 hour, and then infected with H3N2, H1N1pdm, and H1N1 (laboratory strain) influenza virus strains so that the infectivity titer Moi=0.001, and incubated for 1 hour. The washing procedure with SFM was performed, Bax inhibitors (Bax inhibitor peptide (V5) (Val-Pro-Met-Leu-Lys (SEQ ID NO: 1) and (P5) (Pro-Met-Leu-Lys-Glu (SEQ ID NO: 2); manufactured by TOCRIS bioscience)) were added at a concentration of 1.0 μM, which was cultured for 23 hours. The culture supernatant was collected at 24 hours after infection, and the HA titer of the influenza viruses was measured by HA assay (FIG. 4).

The results of this examination demonstrated that the addition of the Bax inhibitor increases the HA titer of the H3N2, H1N1pdm, and H1N1 (laboratory strain) influenza virus strains even under condition of a low concentration as compared with that in Example 2. In addition to this, the increase in the HA titer of the influenza virus was also observed with SEQ ID NO: 2.

Figure 5:
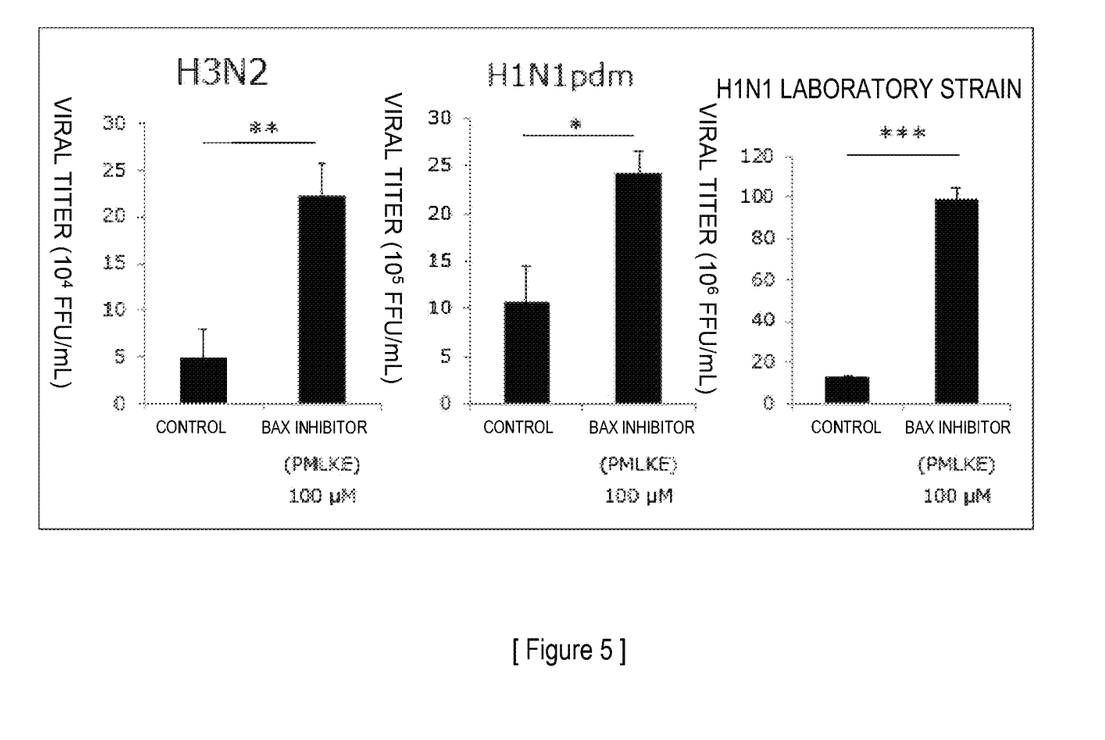
FIG. 5 shows the effect of promoting the proliferation of influenza virus under low Bax inhibitor concentration conditions.

(2) The amount of influenza virus was quantified by focus assay as in Example 2(2) using the culture supernatant at 24 hours after infection to which SEQ ID NO: 2 was added (FIG. 5).

The results of this examination demonstrated that the addition of the Bax inhibitor of SEQ ID NO: 2 enhances the virus proliferation capacity of H3N2, H1N1pdm, and H1N1 (laboratory strain) influenza virus strains.

Example 4 Examination of Effect of Promoting Proliferation of Influenza B Virus by Bax Inhibitor (2 Types)

Figure 6:
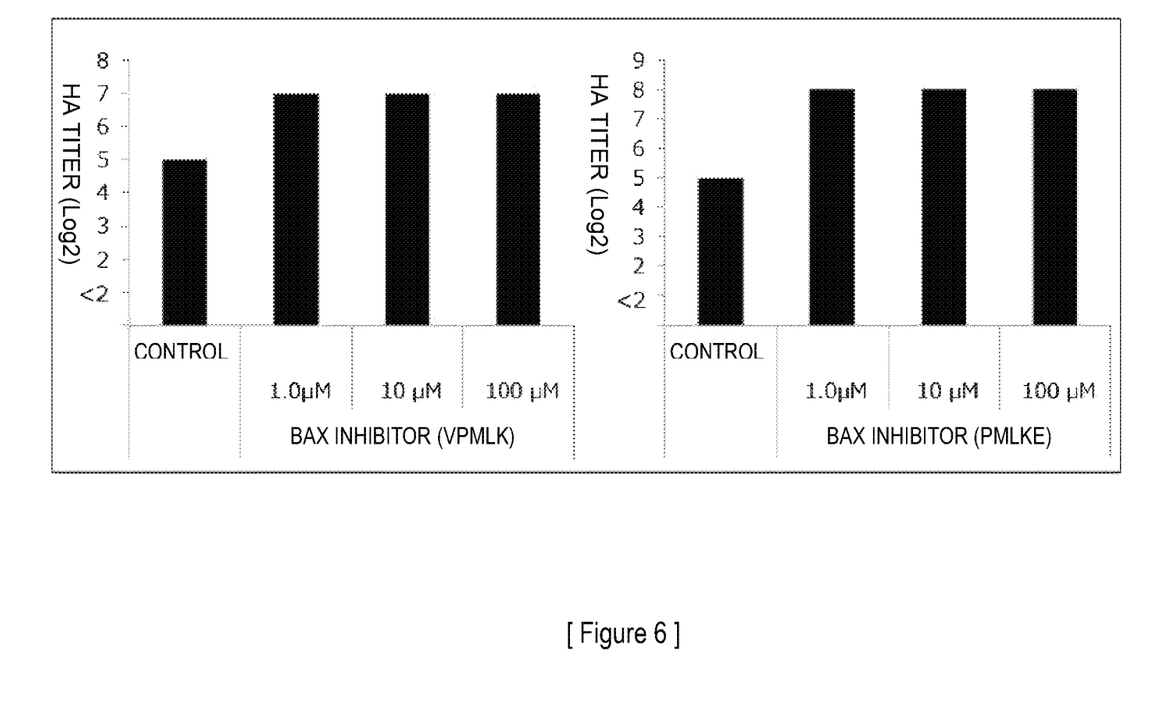
FIG. 6 shows the influenza B virus HA titer under Bax inhibitor concentration conditions.

(1) As in Example 3, the virus strain to be used was changed to an influenza B virus strain (B/Lee/1940) and the virus proliferation capacity was evaluated. Cells were infected with the influenza B virus so that Moi=0.01, and incubated for 1 hour. Thereafter, the washing procedure with SFM was performed, Bax inhibitors (Bax inhibitor peptide (V5) (Val-Pro-Met-Leu-Lys (SEQ ID NO: 1) and (P5) (Pro-Met-Leu-Lys-Glu (SEQ ID NO: 2); manufactured by TOCRIS bioscience)) were added at a concentration of 0 to 100 μM, which was cultured for 47 hours. The culture supernatant was collected at 48 hours after infection, and the HA titer of the influenza virus was measured by HA assay (FIG. 6).

The results of this examination demonstrated that the addition of the Bax inhibitor increases the HA titer of the influenza B virus strain.

Figure 7:
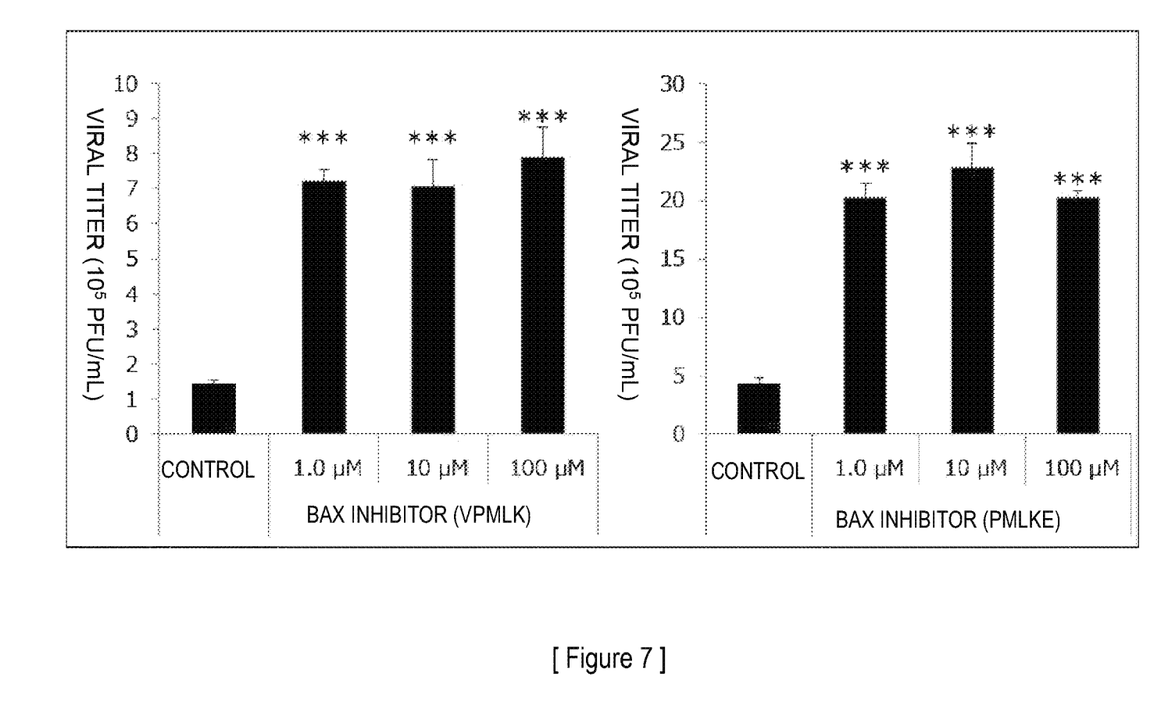
FIG. 7 shows the effect of promoting the proliferation of influenza B virus under Bax inhibitor concentration conditions.

(2) The amount of influenza virus in the culture solution was quantified by the plaque assay described below using the culture supernatant at 48 hours after infection (FIG. 7).

1) Plaque Assay

MDCK cells were cultured in a 12-well plate to reach confluency, washed with PBS, and then conditioned with SFM for 1 hour. The influenza B virus culture supernatant collected at 48 hours after infection was diluted 100 to 100,000-fold, which was added to the MDCK cells cultured in the above 12-well plate at 1 mL/well and incubated for 1 hour, thereby infecting the cells with the influenza B virus. This test was performed in triplicate. After infection, the washing procedure with SFM was performed, SFM containing 0.8%-agarose (Lonza Japan Ltd., SeaKem® Gold Agalose) and 2.0 μg/mL-acetylated trypsin (manufactured by Sigma) was added at 2.0 mL/well, which was cultured for 47 hours. After culture, 1 mL of a mixed solution of ethanol:acetic acid=5:1 was added to each well, which was allowed to stand at 4° C. overnight or longer to immobilize the cells. The immobilized cells were stained with a crystal violet solution with a concentration of 1% (w/v), washed with PBS, and then, the number of portions (plaque) where cells were sloughed off with viral infection was counted.

2) The results of this examination demonstrated that the Bax inhibitors of SEQ ID NO: 1 and SEQ ID NO: 2 also exhibit the effect of enhancing the virus proliferation capacity on influenza B virus strain.

Figure 8:
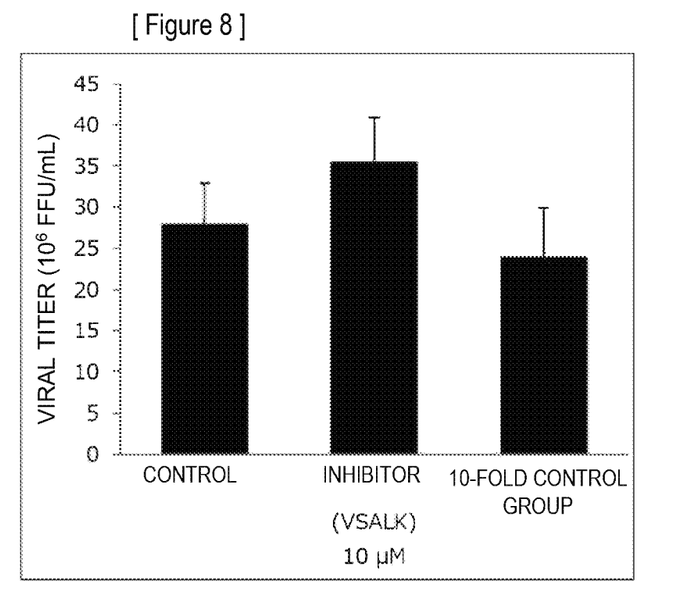
FIG. 8 shows the effect of promoting the proliferation of influenza virus under Bax inhibiting conditions (embryonated chicken egg).

Example 5 Examination of Effect of Promoting Proliferation of Influenza Virus by Bax Inhibitor in Embryonated Chicken Eggs (1) 11-day old embryonated chicken eggs were used to evaluate the proliferation capacity of an H1N1 influenza virus strain (A/Puerto Rico/8/1934). The control group was infected with the H1N1 influenza virus so that the 50% egg infection dose ($EID_{50}$) can be $5\times10^2$ $EID_{50}$/chicken egg, and the 10-fold control group was infected so that it can be $5\times10^3$ $EID_{50}$/chicken egg. For the Bax inhibitor group (the group added with Val-Ser-Ala-Leu-Lys (SEQ ID NO: 7)), the above peptide was added to the virus solution so that the final concentration of the Bax inhibitor can be 10 μM when the amount of allantoic fluid of the chicken eggs was defined as 5 mL, thereby performing infection procedures. The infection fluid volume was 200 μL/chicken egg in each group. The allantoic fluid was collected from embryonated chicken eggs at 48 hours after infection, and the amount of influenza virus was quantified by focus assay as in Example 2(2) (FIG. 8). Error bars represent the standard error.

(2) The results of this examination demonstrated that the addition of the Bax inhibitor increases the viral titer of the H1N1 influenza virus strain by 1.27 times. In addition, the results demonstrated that owing to the addition of the Bax inhibitor, the viral titer to be obtained becomes higher than that of the embryonated chicken eggs infected with 10-fold volume of virus.

What is claimed is:

1. A method for proliferating an influenza virus in a host, the method comprising the steps of:
   1. Infecting the host with an influenza virus;
   2. Culturing the influenza virus-infected host of Step 1 under conditions in which the influenza virus replicates; and
   3. Adding a Bax inhibitor to the host, either before the infecting of Step 1, or after the infecting of Step 1, or simultaneously with the infecting of Step 1, wherein the Bax inhibitor inhibits transfer of Bax to the host's inner mitochondrial membrane;

wherein the host is an embryonated chicken egg or a cultured cell that is susceptible to the influenza virus.

2. The method according to claim 1, wherein the Bax inhibitor is added to the host after the infecting of Step 1.

3. The method according to claim 1, wherein the Bax inhibitor is a peptide selected from the group consisting of Val-Pro-Met-Leu-Lys (SEQ ID NO: 1), Pro-Met-Leu-Lys-Glu (SEQ ID NO: 2), Val-Pro-Thr-Leu-Lys (SEQ ID NO: 3), Val-Pro-Ala-Leu-Arg (SEQ ID NO: 4), Val-Pro-Ala-Leu-Lys (SEQ ID NO: 5), Pro-Ala-Leu-Lys-Asp (SEQ ID NO: 6), Val-Ser-Ala-Leu-Lys (SEQ ID NO: 7), and Ser-Ala-Leu-Lys-Asp (SEQ ID NO: 8).

4. The method according to claim 1, wherein the host is a cultured cell that is susceptible to the influenza virus.

5. A method for preparing influenza virus particles, comprising the steps of:
   1. Infecting the host with an influenza virus;
   2. Culturing the influenza virus-infected host of Step 1 under conditions in which the influenza virus replicates;
   3. Adding a Bax inhibitor to the host, either before the infecting of Step 1, or after the infecting of Step 1, or simultaneously with the infecting of Step 1, wherein the Bax inhibitor inhibits transfer of Bax to the host's inner mitochondrial membrane; and
   4. Collecting influenza virus particles from the culture after completion of the culturing of Step 2;

wherein the host is an embryonated chicken egg or a cultured cell that is susceptible to the influenza virus.

6. The method according to claim 5, further comprising preparing an influenza vaccine with the influenza virus particles.

7. The method of claim 1, wherein the Bax inhibitor is added to the host before the infecting of Step 1.

8. The method of claim 1, wherein the Bax inhibitor is added to the host simultaneously with the infecting of Step 1.

9. The method according to claim 1, wherein the host is an embryonated chicken egg.

* * * * *

SEQUENCE LISTING

```
<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Val Pro Met Leu Lys
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Pro Met Leu Lys Glu
1               5
```

-continued

```
<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Val Pro Thr Leu Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Val Pro Ala Leu Arg
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Val Pro Ala Leu Lys
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Pro Ala Leu Lys Asp
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Val Ser Ala Leu Lys
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Ser Ala Leu Lys Asp
1               5
```